US012618017B2

(12) United States Patent
Cuoq et al.

(10) Patent No.: US 12,618,017 B2
(45) Date of Patent: May 5, 2026

(54) APPLICATION OF SURFMERS TO MITIGATE FOULING IN OLEFINS PLANTS

(71) Applicant: SABIC GLOBAL TECHNOLOGIES B.V., Bergen Op Zoom (NL)

(72) Inventors: Fabrice Cuoq, Geleen (NL); Martijn Frissen, Geleen (NL); Sharankumar G. Shetty, Bangalore (IN)

(73) Assignee: SABIC Global Technologies B.V., Bergen op Zoom (NL)

( * ) Notice: Subject to any disclaimer, the term of this patent is extended or adjusted under 35 U.S.C. 154(b) by 341 days.

(21) Appl. No.: 18/246,963

(22) PCT Filed: Sep. 27, 2021

(86) PCT No.: PCT/IB2021/058808
§ 371 (c)(1),
(2) Date: Mar. 28, 2023

(87) PCT Pub. No.: WO2022/070020
PCT Pub. Date: Apr. 7, 2022

(65) Prior Publication Data

US 2023/0407196 A1 Dec. 21, 2023

Related U.S. Application Data

(60) Provisional application No. 63/085,980, filed on Sep. 30, 2020.

(51) Int. Cl.
*C10G 75/00* (2006.01)
*C07C 4/04* (2006.01)
*C10G 75/04* (2006.01)

(52) U.S. Cl.
CPC ................ *C10G 75/04* (2013.01); *C07C 4/04* (2013.01)

(58) Field of Classification Search
CPC .......... C10G 9/002; C10G 9/36; C10G 75/04; C02F 5/12; C02F 2303/14; C02F 2305/04;
(Continued)

(56) References Cited

U.S. PATENT DOCUMENTS 5,266,186 A 11/1993 Kaplan
5,420,194 A * 5/1995 Rowe ....................... C10G 9/00 524/517
(Continued)

FOREIGN PATENT DOCUMENTS

CN 107720982 2/2018
EP 1937726 7/2008

OTHER PUBLICATIONS

Polymerisable surfactants (surfmers) for emulsion polymerisation production, Surfactants in Polymers, Coatings Inks and Adhesives, Chapter 3, Alain Guyot, Andris Zicmanis (2003). (Year: 2003).*
(Continued)

*Primary Examiner* — Prem C Singh
*Assistant Examiner* — Brandi M Doyle
(74) *Attorney, Agent, or Firm* — Norton Rose Fulbright US LLP

(57) ABSTRACT

A method for reducing fouling in an aqueous system of an olefin production plant is disclosed. The method includes adding an effective amount of a surfmer to the aqueous system, wherein the surfmer forms a water soluble adduct by covalently bonding to one or more fouling precursor compounds formed during olefin production.

18 Claims, 4 Drawing Sheets

(58) Field of Classification Search
CPC ... C02F 2103/365; C02F 2303/22; C07C 4/04
See application file for complete search history.

(56) References Cited

U.S. PATENT DOCUMENTS

| | | | | |
|---|---|---|---|---|
| 5,427,690 | A | 6/1995 | Rowe et al. | |
| 2014/0263078 | A1 | 9/2014 | Gill et al. | |
| 2016/0010006 | A1 | 1/2016 | Subbiah et al. | |
| 2016/0039753 | A1 | 2/2016 | Ng et al. | |
| 2017/0183248 | A1* | 6/2017 | Leen | C02F 5/12 |

OTHER PUBLICATIONS

Dorr, et al. "The styrene-maleic acid copolymer: a versatile tool in membrane research", *Eur Biophys J*, 45: 3-21, 2016.

GPS Safety Summary, "4-Hydroxy-TEMPO", version 001, pp. 1-6, 2014.

International Search Report and Written Opinion issued in corresponding International Application No. PCT/IB2021/058808 mailed Dec. 20, 2021.

Scheidelaar, et al. "Effect of Polymer Composition and pH on Membrane Solubilzation by Styrene-Maleic Acid Copolymers", *Biophysical Journal*, 111, pp. 1974-1986, 2016.

Summers, et al. "Applications of polymerizable surfactants", *Advances in Colloid and Interface Science*, 100-102, pp. 137-152, 2003.

Veregin, et al. "Molecular Weight Distributions in Nitroxide-Mediated Living Free Radical Polymerization: Kinetics of the slow equilibria between growing and dormant chains", *Macromolecules*, 29, 3346-3352, 1996.

* cited by examiner

APPLICATION OF SURFMERS TO MITIGATE FOULING IN OLEFINS PLANTS

CROSS REFERENCE TO RELATED APPLICATIONS

This application is a national phase under 35 U.S.C. § 371 of International Application No. PCT/IB2021/058808, filed Sep. 27, 2021, which claims the benefit of priority to U.S. Provisional Patent Application No. 63/085,980, filed Sep. 30, 2020, the entire contents of each of which are hereby incorporated by reference in their entirety.

FIELD OF INVENTION

The invention generally concerns reducing fouling in an olefin production plant. In particular, the invention can include using a surfmer to reduce fouling in an aqueous system of an olefin production plant.

BACKGROUND OF THE INVENTION

Olefins are common building blocks for a variety of petrochemicals. One way of producing olefins is to steam crack hydrocarbon feedstocks such as naphtha, liquid petroleum gas (LPG), ethane, propane and/or butane. In the steam cracking (pyrolysis) process, the hydrocarbons are superheated in a reactor to temperatures as high as 750-950° C. For the cracking process, a dilution steam generator (DSG) supplies dilution steam to the reactor to reduce the partial pressure of the hydrocarbons. The heated hydrocarbons are then rapidly cooled (quenched) to stop the reactions after a certain point to optimize cracking product yield. The quenching of the heated gas in many processes is carried out using water in a quench water tower (QWT). The heated cracked gas (including olefins) is flowed into the bottom of the quench water tower and, at the same time, water is sprayed into the top of the quench water tower. As the water in the quench water tower falls, it makes contact with the upwardly flowing heated cracked gas and, in that way, cools the heated cracked gas (that includes olefins) and dilution steam.

Because of the direct contact between the heated cracked gas in the quench water tower and the condensation of the dilution steam, the water flowing from the quench water tower is mixed with condensed hydrocarbons (e.g., pyrolysis gasoline). In the quench water tower, the pyrolysis gasoline and water mixes and can form an emulsion. Thus, the quench water tower effluent stream flowing from the bottom of the quench water tower may include an emulsion having a hydrocarbon phase dispersed in a continuous water phase. Hydrocarbon in water emulsions are particularly difficult to break. In other words, the emulsion is stable because, once the emulsion is formed, the water does not easily separate from the pyrolysis gasoline.

To facilitate the separation of the water from the pyrolysis gasoline, the quench water tower effluent stream is flowed from the quench water tower to a quench water settler (QWS). At the quench water settler, the quench water effluent stream (including the emulsion) is settled and water is drawn off from the quench water settler. Then, the water from the quench water settler is sent to a process water stripper (PWS). The process water stripper strips the water of acid gases and dissolved hydrocarbons. After being stripped in the process water stripper, the water is routed to the dilution steam generator (mentioned above). The water that is used to generate dilution steam for the cracking furnaces, and subsequently condensed in the quench water tower, then circulated to the quench water settler, then to the process water stripper, and finally back to the dilution steam generator can be oftentimes be referred to as process water, which circulates in a quench water tower loop. The quench water tower, quench water settler, process water stripper, and dilution steam generator can be collectively referred to as a dilution steam system (DSS).

Because the emulsion in the quench water tower tends to be stable, the attempt to separate pyrolysis gasoline and various other contaminants formed as a result of the pyrolysis from water in the quench water tower and/or quench water tower settler is often ineffective and can be time consuming and costly. Consequently, the process water may carry a large amount of fouling precursors, for example reactive monomeric species, to the process water stripper, which causes fouling of the process water stripper. The dilution steam generator can also get fouled because of hydrocarbons carry-over and subsequent polymerization. The conditions at which the dilution steam is generated is effective for continued reactions between the fouling precursors. Further, process water that flows from the bottom of the quench water tower and the quench water settler can contain traces of fouling precursors such as styrene as well as oligomers of styrene that form in the water as a result of the long residence time of the water recycle in the quench water tower loop. These oligomers can grow further at process water stripper conditions and can cause fouling in the dilution steam system.

Fouling at the dilution steam system, such as at a bottom of the process water stripper and in the dilution steam generator preheaters, can lead to poor energy efficiency and, in a worst case scenario, to a plant shutdown, if excessive fouling sufficiently restricts flow of process water in the quench water tower loop. Many olefin cracking units suffer from poor quench/process water quality because of fouling. Fouling can also occur in other aqueous systems of an olefin production plant where radical reactions are expected. Fouling is one of the key performance issues in olefins plant operations.

Currently, fouling is primarily addressed by dosing dispersants or polymerization inhibitors and adding an emulsion breaker upstream the dilution steam system. Dispersants can disperse the fouling precursors by getting physically adsorbed onto the surface of the fouling precursors. The physical adsorption or bond can generally get weakened and break at high temperatures, such as at temperatures used for generating dilution steam. This makes the process of fouling reduction in olefin production plant by adding dispersants less efficient. For example, US20140263078A1 teaches reducing fouling in equipment used during recovering hydrocarbons from crude oil or bituminous sands. Fouling is reduced by dispersing the foulants, by adding slit dispersants, and hydrocarbon dispersants.

BRIEF SUMMARY OF THE INVENTION

A discovery has been made that provides a solution to some of the aforementioned problems associated with fouling in an aqueous system of an olefin production plant. In particular, the solution can be premised on using surfmers to reduce fouling in a dilution steam system and/or other aqueous systems of an olefin production plant that produces olefins by steam cracking.

Embodiments of the present invention include a method for reducing fouling in an aqueous system of an olefin production plant. The method can include adding an effective amount of a surfmer to the aqueous system, wherein the surfmer forms a water soluble adduct by covalently bonding to one or more fouling precursor compounds formed during olefin production. The covalent bond is significantly stronger than electrostatic or other non-covalent bonding interactions that are common for classical dispersants. The water soluble adduct can be stable at high temperatures, such as at temperatures used to generate dilution steam to be used for hydrocarbon cracking. The olefin production plant can produce olefins by steam cracking of a hydrocarbon feed. In some aspects, the hydrocarbon feed can be naphtha, LPG, ethane, propane, butane or any combination thereof. In some aspects, the olefin can be ethylene, propylene or both. The aqueous system can be a dilution steam system. The water soluble adduct can be a water soluble polymer. In some aspects, amount of the fouling precursor compound present in an aqueous system can be determined, and weight ratio of the surfmer added to the fouling precursor compound present in the aqueous system can be 0.25:1 to 1.2:1. In some aspects, amount of styrene present in an aqueous system can be determined, and weight ratio of the surfmer added to styrene present in the aqueous system can be 0.25:1 to 1.2:1. In some aspects, amount of styrene present in a dilution steam system can be determined, and weight ratio of the surfmer added to styrene present in the dilution steam system can be 0.25:1 to 1:1. Non-limiting examples of fouling precursor compounds can be styrene, indene, divinylbenzene, methyl styrene, cyclopentadiene, or any combination thereof. In some aspects, the water soluble adduct can be removed from the aqueous system. In some aspects, the water soluble adduct can be removed from the process water of the dilution steam system by a blow-down process. Surfmers of the present invention can preferentially polymerize with the fouling precursors compared to self-polymerization. In some aspects, the surfmer can be maleic acid, maleic anhydride, polyethylene glycol (PEG) functionalized maleamide, PEG-polypropylene glycol (PPG) block copolymer functionalized maleamide, or any combination thereof. In some particular aspects, the PEG functionalized maleamide can have a chemical structure of Formula I or Formula II Formula I

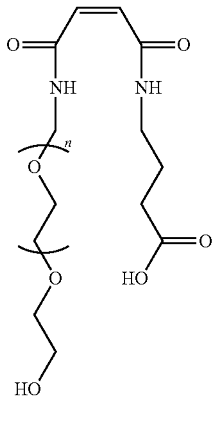

-continued

Formula II

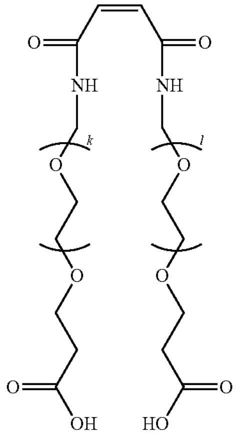

where n in Formula I can be 0, 1, 2, 3, 4, 5, 6, 7, 8, 9 or 10; k and l in Formula II can be independently 0, 1, 2, 3, 4, 5, 6, 7, 8, 9 or 10.

A surfmer can be added via a feed, condenser water, direct injection, a slip stream, or any combination thereof. The surfmer can be added at any location of an aqueous system, as will be appreciated by those of skill. In some aspects, a surfmer can be added to a process water of a dilution steam system. In some aspects, a surfmer can be added to a process water of a dilution steam system in the feed of such process where there is no free gasoline present. In some particular aspects, a surfmer can be added to the process water at a process water stripper unit of the dilution steam system. In some particular aspects, a surfmer can be added to the process water at a bottom portion of the process water stripper unit.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %," or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective" as is used in the specification and/or claims, means adequate to accomplish a desired, expected, or intended result.

The term "effective amount" as is used herein, is an amount of a surfmer that is, when added to an aqueous system of a olefin production plant, sufficient to produce a statistically significant, measurable decrease in fouling of the aqueous system as compared to fouling in the aqueous system when the surfmer is not added or used.

The terms and phrases "fouling precursors," "fouling precursor compounds," or "foulants" as used interchangeably herein, refer to reactive monomeric species that can be formed in the furnaces and/or present in an aqueous system of an olefin production plant that produces olefins by steam cracking. The fouling precursors can polymerize under process conditions used for olefin production and form water insoluble polymers. The term "fouling" in an aqueous system refers to presence of fouling precursor compounds, water insoluble oligomers and/or polymers of the fouling precursor compounds in the aqueous system.

The terms "surfmer" and "surfmers" as is used herein, refer to polymerizable surfactant(s). Surfmers are surfactant monomers that can polymerize.

Pyrolysis gasoline is a pyrolysis by product that is less dense than water. Pyrolysis gasoline can include paraffins, aromatics, olefins, and/or diolefins, or any combination thereof. In some aspects, pyrolysis gasoline can include C5 to C12 paraffins, aromatics, olefins, and/or diolefins, or combinations thereof. In some particular aspects, pyrolysis gasoline can include styrene, isoprene, piperylenes, cyclopentadienes, indene, divinylbenzene, methyl styrene or any combination thereof.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification. In one particular aspect, and with respect to "consist essentially of," a basic and novel characteristic of the present invention can include the use of a surfmer(s) to reduce fouling in an aqueous system of an olefin production plant.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Figure 1:
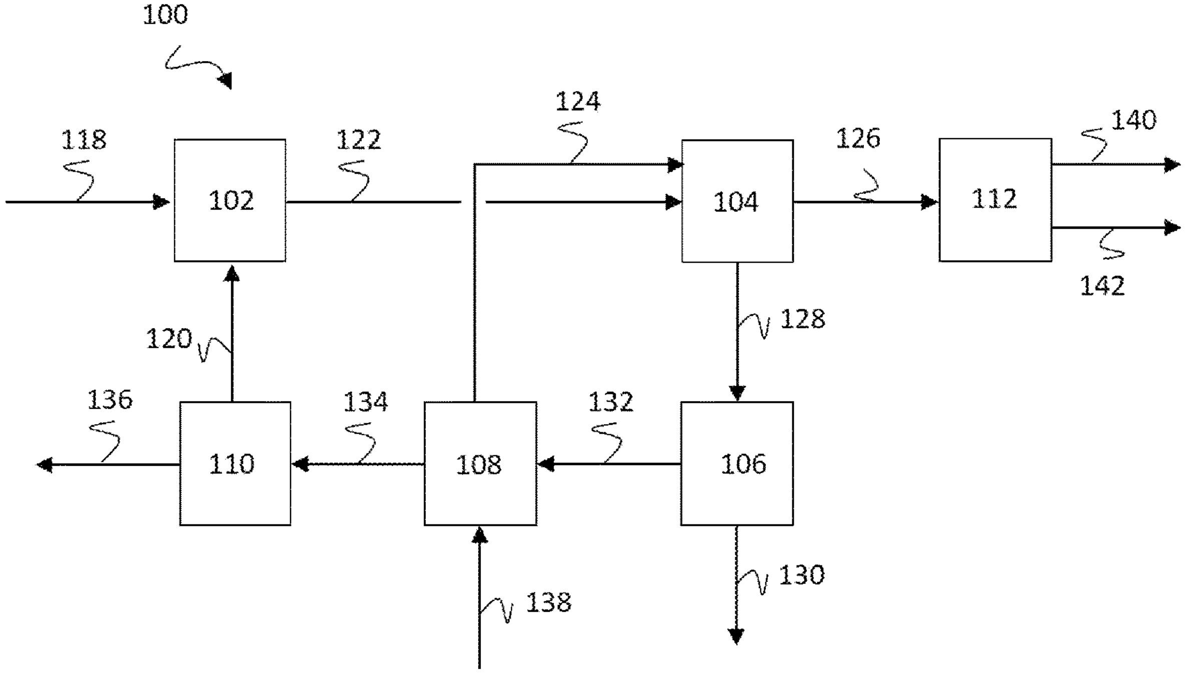
FIG. 1: Schematic representation of a method of the present invention to produce olefin.

A discovery has been made that provides a solution to at least some of the aforementioned problems associated with fouling in an aqueous system of olefins production plant. In one aspect, a solution can include adding an effective amount of a surfmer to the aqueous system, wherein the surfmer can form a water soluble adduct by covalently bonding to a fouling precursor compound formed during olefin production. The olefins production plant can be a pyrolysis plant and can produce olefins by steam cracking of a hydrocarbon feed. The methods of the present invention are capable of reducing fouling in devices and aqueous solutions of the aqueous system, such as in devices and process water of a dilution steam system. Presence of surfmers in an aqueous solution of an aqueous system reduce fouling in surfaces that come in contact with the aqueous solution during the olefin production process. In some aspects, surfmers of the present invention can reduce fouling that occurs due to the presence of pyrolysis gasoline, and/or emulsion containing pyrolysis gasoline and water in the process water of a dilution steam system.

These and other non-limiting aspects of the present invention are discussed in the following sections.

A. Surfmers

Surfmers of the present invention can contain a polar functional group. The polar functional group can be carboxyl group, hydroxyl group, amide group, ester group, ether group or any combination thereof. In some aspects, the surfmer can be maleic acid, maleic anhydride, PEG functionalized maleamide, PEG-PPG block co-polymer functionalized maleamide or combinations thereof. In some particular aspects, average molecular weight of the PEG functionalized maleamide, or PEG-PPG block co-polymer functionalized maleamide can be 200 g/mol to 5000 g/mol or at least any one of, equal to any one of, or between any two of 200 g/mol, 400 g/mol, 600 g/mol, 800 g/mol, 1000 g/mol, 1200 g/mol, 1400 g/mol, 1600 g/mol, 1800 g/mol, 2000 g/mol, 2200 g/mol, 2400 g/mol, 2600 g/mol, 2800 g/mol, 3000 g/mol, 3200 g/mol, 3400 g/mol, 3600 g/mol, 3800 g/mol, 4000 g/mol, 4200 g/mol, 4400 g/mol, 4600 g/mol, 4800 g/mol and 5000 g/mol. In some aspects, the PEG functionalized maleamide can be a compound having a chemical structure of Formula I or Formula II. In some aspects, the surfmer can be maleic acid. In some aspects, the surfmer can be maleic anhydride. In some aspects, the surfmer can be PEG functionalized maleamide. In some aspects, the surfmer can be PEG-PPG block co-polymer functionalized maleamide. In some aspects, the surfmer can be a combination of surfmers mentioned herein. Non limiting combination can include:

maleic acid, with at least one of maleic anhydride, PEG functionalized maleamide, and PEG-PPG block co-polymer functionalized maleamide;
maleic anhydride, with at least one of maleic acid, PEG functionalized maleamide, and PEG-PPG block co-polymer functionalized maleamide;
PEG functionalized maleamide, with at least one of maleic acid, maleic anhydride, and PEG-PPG block co-polymer functionalized maleamide; and/or
PEG-PPG block co-polymer functionalized maleamide with at least one of maleic acid, maleic anhydride, and PEG functionalized maleamide.

A surfmer of the present invention can get covalently bonded to a fouling precursor compound formed during olefin production by steam cracking of a hydrocarbon, and can form a water soluble adduct. In some aspects, the covalent bond can be a carbon carbon covalent bond. In some aspects, the water soluble adduct can be a water soluble polymer. In some aspects, the water soluble polymer can be a polymer formed by polymerization of surfmer monomers and fouling precursor compound monomers, and/or a polymer formed by a surfmer getting covalently bonded to a polymer of the fouling precursor compounds.

B. Method of Producing Olefin

In one aspect of the present invention a method for producing olefins is described. The method can include steam cracking of a hydrocarbon feed to obtain a cracked gas containing an olefin, quenching and purifying the cracked gas to obtain purified olefin, and adding a surfmer to an aqueous system used in quenching and/or purifying the cracked gas. In some aspects, the cracked gas can contain a mixture of olefins. Referring to FIG. 1, a system and a method to produce an olefin is described. System 100 can include units such as a steam cracking unit 102, a quench water tower (QWT) 104, a quench water settler (QWS) 106, a process water stripper (PWS) 108, a dilution steam generator (DSG) 110, and unit 112. In some aspects, the unit 112 can include a compressor. A hydrocarbon stream 118 can be fed to the steam cracking unit 102 and can get cracked at a temperature 600° C. to 1000° C. to form heated cracked gas and pyrolysis gasoline. Cracking in the steam cracking unit 102 can be performed in presence of a dilution steam to lower hydrocarbon partial pressures. The DSG 110 can supply the dilution steam to the steam cracking unit 102 via a stream 120. A stream 122 containing the heated cracked gas along with pyrolysis gasoline and dilution steam can be fed to a bottom portion of the QWT 104. In the QWT 104 the stream 122 can be contacted with a water stream 124 and the heated cracked gas can get cooled, the dilution stream can get condensed and at least a portion of the pyrolysis gasoline can get mixed with water to form an emulsion. A stream 126 containing cooled cracked gas can be directed to the unit 112 from the QWT 104. A stream 128 containing pyrolysis gasoline and water mixes containing pyrolysis gasoline, water and/or pyrolysis gasoline-water emulsions can be fed to the QWS 106 from the QWT 104. Water and the pyrolysis gasoline can be separated in the QWS 106. A stream 130 containing the pyrolysis gasoline can exit the QWS 106. The pyrolysis gasoline stream 130 can be subjected to further processing steps (not shown). A stream 132 containing water can be fed to the PWS 108 from the QWS 106. The water of the stream 132 can contain dissolved hydrocarbons and acid gases. At least a portion of the dissolved acid gases and hydrocarbons can be separated from the water in the PWS 108 to form stripped water. A stream 134 containing stripped water can be fed to the DSG 110 from the PWS 108. The DSG 110 can generate the dilution steam and the stream 120 containing the dilution steam can be fed to the steam cracking unit 102. A stream 136 containing a portion of water in the DSG 110 can be sent to a water treatment plant (not shown). The water that is used to generate dilution steam for steam cracking, and subsequently condensed in the QWT 104, then circulated to the QWS 106, then to the PWS 108, and finally back to the DSG 110 is referred to as the process water. The QWT 104, QWS 106, PWS 108 and DSG 110 are collectively referred to as the dilution steam system. A surfmer, according to the methods of the present invention, can be added to the DSS. In some aspects, a surfmer can be fed to PWS 108. In some particular aspects, a surfmer 138 can be fed at the bottom portion of the PWS 108.

The cooled cracked gas from the QWT 104 can be directed to further processing steps such as compression, purification, drying, and/or separation in the unit 112 to obtain polymer grade olefins. In some aspects, the unit 112 can include one or more compression unit, caustic tower, drying unit, cold box, separation columns and units and/or cooling tower. In some aspects, compression of the cooled cracked gas can be performed over multiple stages and compression unit can include multiple compression units. In some aspects, the separation columns and units can include demethanizer column, deethanizer column, C2-splitter, depropanizer column, and/or C3-splitter. In some aspects, a stream 140 containing polymer grade ethylene can be obtained from unit 112. In some aspects, a stream 142 containing polymer grade propylene can be obtained from unit 112. In some aspects, a stream 140 containing polymer grade ethylene and a stream 142 containing polymer grade propylene can be obtained from unit 112. It is contemplated in the context of the present invention that other olefins can also be obtained.

The surfmer addition can be performed by any method known in the art, non-limiting methods include spraying, dripping or pouring. Amount of a surfmer added can be adjusted based on the hydrocarbon feed, olefin plant operation conditions, foulants present or formed during the olefin production process or any combination thereof. In some aspects, amount of surfmer added is adjusted based on turbidity of the process water of the dilution steam system. In some aspects, amount of a fouling precursor compound present in an aqueous system can be determined, and weight ratio of a surfmer added to the fouling precursor compounds present in the aqueous system is 0.25:1 to 1.2:1 or at least any one of, equal to any one of, or between any two of 0.25:1, 0.3:1, 0.4:1, 0.5:1, 0.6:1, 0.7:1, 0.8:1, 0.9:1, 1:1, 1.1:1 and 1.2:1. In some aspects, amount of styrene present in an aqueous system can be determined, and weight ratio of a surfmer added to styrene present in the aqueous system is 0.25:1 to 1.2:1 or at least any one of, equal to any one of, or between any two of 0.25:1, 0.3:1, 0.4:1, 0.5:1, 0.6:1, 0.7:1, 0.8:1, 0.9:1, 1:1, 1.1:1 and 1.2:1. In some aspects, amount of styrene present in a dilution steam system can be determined, and weight ratio of a surfmer added to styrene present in the dilution steam system is 0.25:1 to 1:1 or at least any one of, equal to any one of, or between any two of 0.25:1, 0.3:1, 0.4:1, 0.5:1, 0.6:1, 0.7:1, 0.8:1, 0.9:1, and 1:1. In some aspects, a surfmer can be added by dosing continuously. In some aspects, the dosing rate can be adjusted depending on the fouling precursor concentration in the aqueous system.

In some aspects, a surfmer can be added to the process water of the dilution steam system to a target concentration about 1 ppm to 1000 ppm or at least any one of, equal to any one of, or between any two of 1 ppm, 5 ppm, 10 ppm, 20 ppm, 30 ppm, 40 ppm, 50 ppm, 60 ppm, 70, 80, 90, 100, 200, 300, 400, 500, 600, 700, 800, 900, and 1000 ppm. In some aspects, an aqueous solution and/or a dispersion of surfmer in water is formed and the solution or dispersion is added to an aqueous system. In some particular aspects, the aqueous solution or dispersion of the surfmer can contain 1 wt. % to 70 wt. % or at least any one of, equal to any one of, or between any two of 1 wt. %, 2 wt. %, 5 wt. %, 10 wt. %, 20 wt. %, 30 wt. %, 40 wt. %, 50 wt. %, 60 wt. % and 70 wt. % of the surfmer. In some aspects, reduction in fouling obtained by the methods of the present invention can be evidenced by operational change of pressure in the PWS 108 and/or logarithmic mean temperature difference (LMTD) of the heat exchangers of the system In some aspects, the water soluble adduct formed by addition of a surfmer can be removed from the aqueous system. In some aspects, the water soluble adduct can be removed from the process water by a blow down process from the stream 136 to a water treatment plant.

The units of olefin production process can include one or more heating and/or cooling devices (e.g., insulation, electrical heaters, jacketed heat exchangers in the wall) and/or controllers (e.g., computers, flow valves, automated values, inlets, outlets, etc.) that can be used to control the process temperature and pressure of the reaction and/or process mixture. A single or multiple units can be used. The units can be positioned parallel and/or in series.

As part of the disclosure of the present invention, a specific example is included below. The example is for illustrative purposes only and is not intended to limit the invention. Those of ordinary skill in the art will readily recognize parameters that can be changed or modified to yield essentially the same results.

EXAMPLES

Example 1

Efficiency of Surfmers for Fouling Reduction and Mitigation

Figure 2:
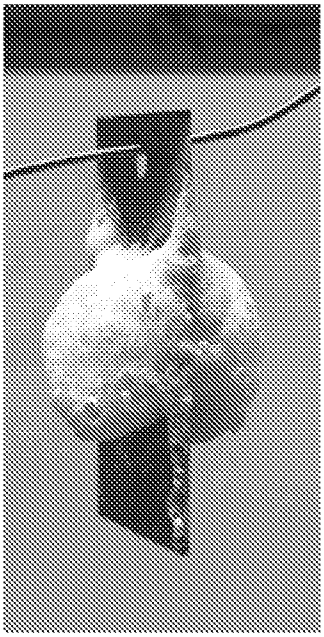
FIG. 2: Polystyrene deposit on a steel carbon coupon, as described in Example 1.
Figure 3:
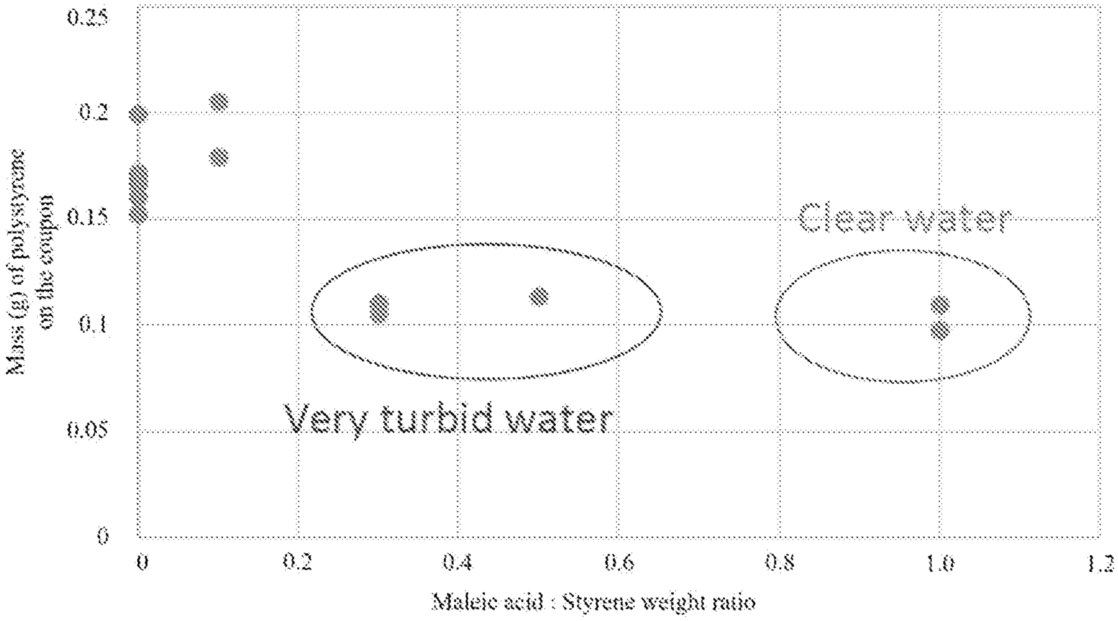
FIG. 3: Mass of polystyrene deposited on a steel carbon coupon with varying weight ratio of maleic acid to styrene added, as described in Example 1.
Figures 4A, 4B:
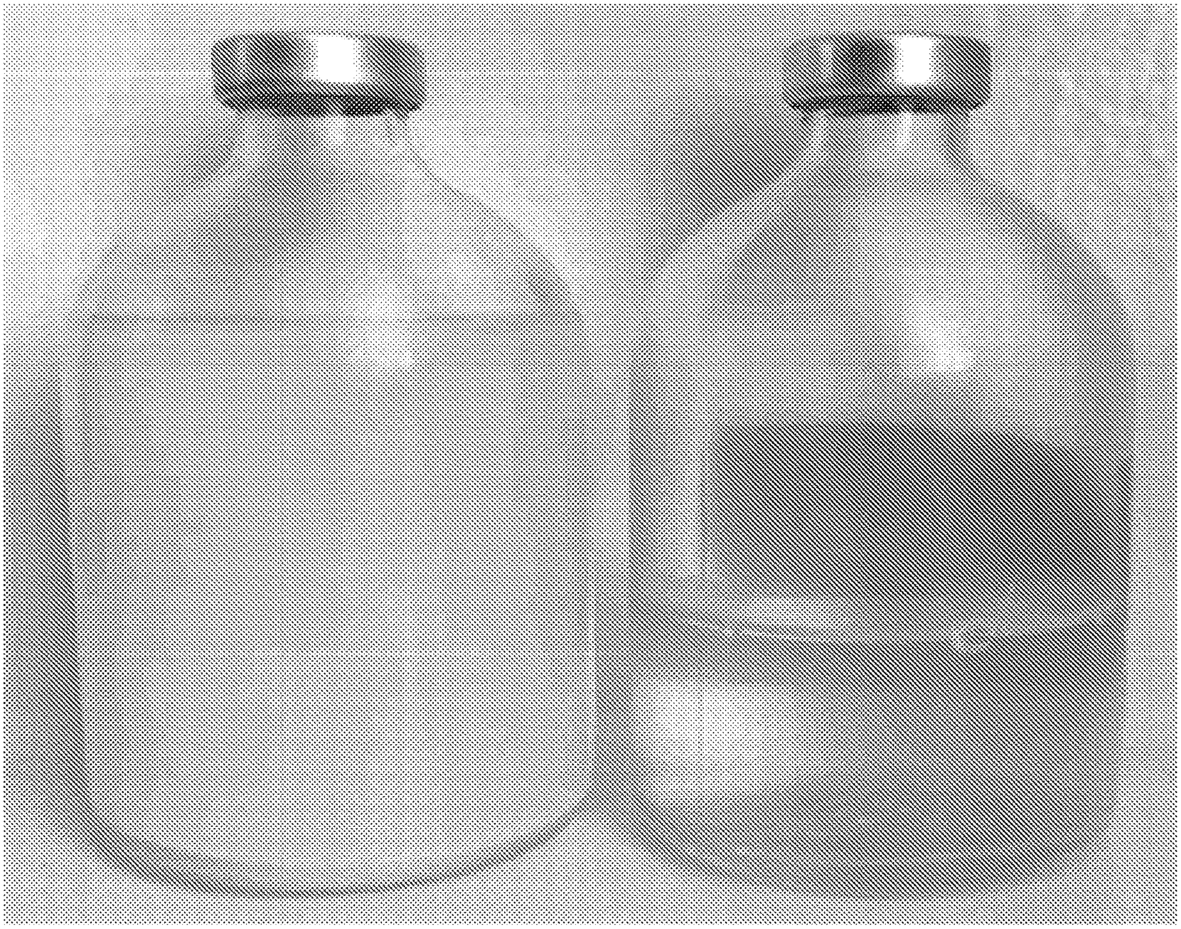
FIG. 4: Process water fouling simulator (PWFS) water phase with weight ratio of maleic acid to styrene 0.3:1 (A) and 1:1 (B), as described in Example 1.

Efficiency of surfmers for fouling reduction and mitigation was assessed with a process water fouling simulator (PWFS). The PWFS contains a 500 ml glass vessel. A total of 400 mL DM water with a pH of 8-9 (increased with monoethanolamine) and a conductivity of ca. 215 μS/cm (increased with NaCl) was introduced in the vessel. A metal coupon made out of carbon steel was hung through the cooler in a way that it was immersed in the water. After 15 min of nitrogen purging, the purging was stopped, a surfmer, maleic acid, was added and the vessel was immersed in the oil bath, which was heated to 140° C. The maleic acid (hydrolysed maleic anhydride solution) was added to the water phase. A total of 8 mL TBC-free styrene was dosed via a perfusor at a rate of 60 mL/h. This styrene contained 7000 ppm of azobisisobutyronitrile (AIBN) which initiated the radical polymerization reaction. Polystyrene formed gets deposited on the coupon (FIG. 2). After 1 h the polymerization was stopped and the coupon was dried overnight at 35° C./vacuum. Once the coupon is dry, it is then weighed and the polystyrene mass is compared to other experiments. A low polystyrene mass indicates an efficient fouling reduction. The water phase after each experiment was also sampled. At maleic acid to styrene weight ratio 0.3:1 the polystyrene mass on the coupon is halved (FIG. 3). The amount of polystyrene on the coupon does not decrease much more at higher maleic acid to styrene weight ratio. It can however be noticed that the water quality is much impacted. Indeed, at a maleic acid to styrene weight ratio of 1:1, the water phase after polymerization is very clear, which means that most of the polystyrene that has been formed was soluble in water (FIG. 4). This indicates that most of the adduct that is formed in the process water stripper could easily flow to the dilution steam generator and end up in the blow down towards the wastewater treatment plant.

Figure 5A:
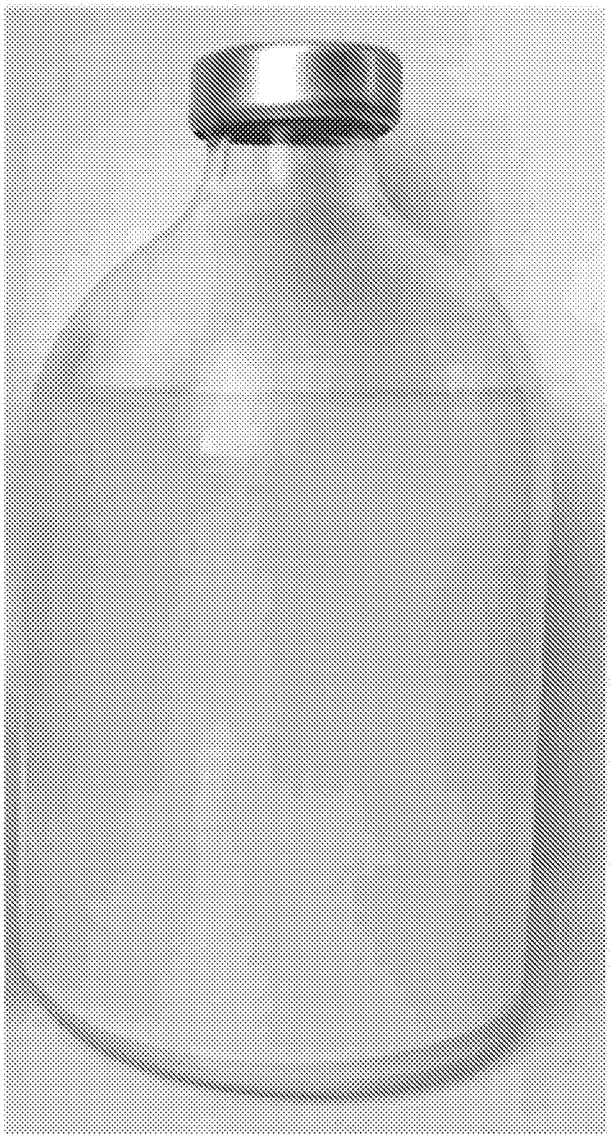
FIGS. 5A-5B: PWFS water phase at high (FIG. 5A) and low (FIG. 5B) pH, with weight ratio of maleic acid to styrene, as described in Example 1.
Figure 5B:
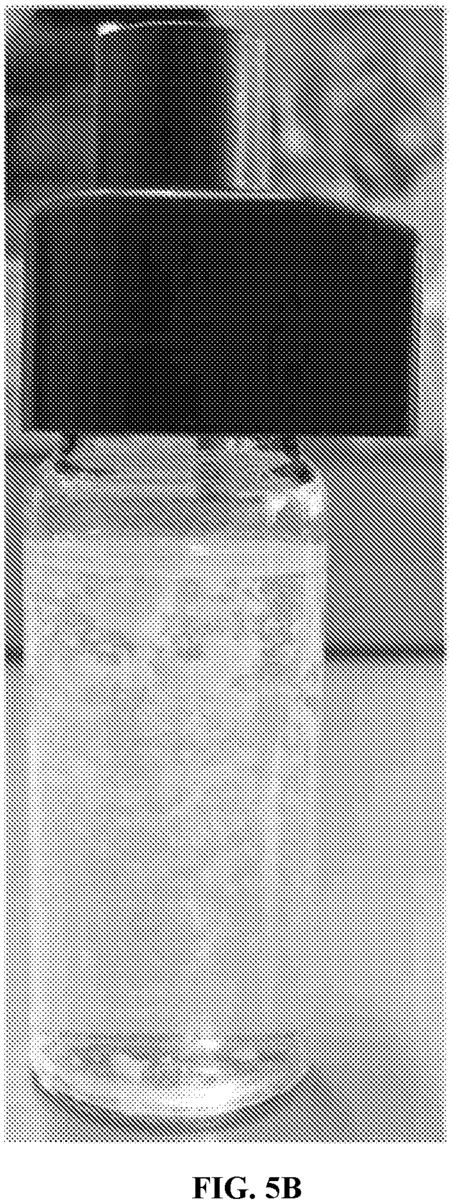

The zeta potential of two different water phases were measured after polymerization. Maleic acid to styrene weight ratio of 0.1:1 led to a zeta potential of −52 mV at pH 8. Zeta potential went down to −11 mV when pH of the solution was decreased with acetic acid. This confirms that the maleic acid is incorporated in the polystyrene backbone. It was also observed that the stability of the polymer was strongly affected by the pH (FIGS. 5A and 5B). The polymer was aggregating at low pH as the maleic acid groups became protonated. Similar results were obtained for maleic acid to styrene weight ratio of 0.01:1.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

In the context of the present invention, at least the following embodiments are described. Embodiment 1 is directed to a method for reducing fouling in an aqueous system of an olefin production plant, the method includes, adding an effective amount of a surfmer to the aqueous system, wherein the surfmer forms a water soluble adduct by covalently bonding to one or more fouling precursor compound(s) formed during olefin production. Embodiment 2 is directed to the embodiment 1, wherein the olefin production plant produces olefin by steam cracking of a hydrocarbon feed. Embodiment 2 is directed to any one of the embodiments 1 or 2, wherein the aqueous system is a dilution steam system. Embodiment 4 is directed to any one of the embodiments 1 to 3, wherein the surfmer is added to a process water stripper unit of the dilution steam system. Embodiment 5 is directed to the embodiment 4, wherein the surfmer is added to a bottom portion of the process water stripper unit. Embodiment 6 is directed to any one of the embodiments 1 to 5, wherein the water soluble adduct is a water soluble polymer. Embodiment 7 is directed to any one of the embodiments 1 to 6, wherein the surfmer is maleic acid, maleic anhydride, polyethylene glycol (PEG) functionalized maleamide, PEG-PPG block co-polymer functionalized maleamide, or any combination thereof. Embodiment 8 is directed to the embodiment 7, wherein the PEG functionalized maleic anhydride has a chemical structure of formula I or formula II. Embodiment 9 is directed to any one of the embodiments 1 to 8, wherein the one or more fouling precursor compounds are styrene, indene, divinylbenzene, methyl styrene, or cyclopentadiene, or any combination thereof. Embodiment 10 is directed to any one of the embodiments 1 to 9, further including removing the water soluble adduct from the aqueous system. Embodiment 11 is directed to embodiment 10, wherein the aqueous system is a dilution steam system and the water soluble adduct is removed from a process water of the dilution steam system by a blow down process. Embodiment 12 is directed to any one of the embodiments 1 to 12, further including determining amount of the fouling precursor compound present in the aqueous system, and adding the surfmer to the aqueous system such that weight ratio of the added surfmer to the fouling precursor compound is 0.25:1 to 1.2:1. Embodiment 13 is directed to the embodiment 12, wherein the fouling precursor compound is styrene. Embodiment 14 is directed to the embodiment 13, wherein weight ratio of the added surfmer to styrene is 0.25:1 to 1:1, and wherein the aqueous system is a dilution steam system. Embodiment 15 is directed to any one of the embodiments 1 to 14, wherein the surfmer is dosed continuously. Embodiment 16 is directed to any one of the embodiments 1 to 15, wherein the hydrocarbon feed is naphtha, liquid petroleum gas, ethane, propane, butane, or any combination thereof. Embodiment 17 is directed to the embodiment 4, wherein the surfmer is added to a process water of the process water stripper unit.

What is claimed is:

1. A method for reducing fouling in an aqueous system of an olefin production plant, the method comprising:

adding an effective amount of a polyethylene glycol (PEG) functionalized maleamide to the aqueous system, wherein the PEG functionalized maleamide forms a water soluble adduct by covalently bonding to one or more fouling precursor compound(s) formed during olefin production, and wherein the PEG functionalized maleamide has a chemical structure of formula I or formula II, Formula I

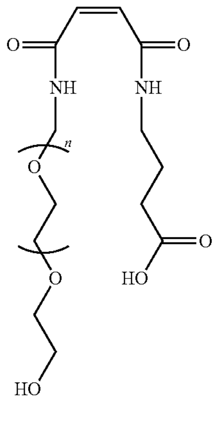

-continued

Formula II

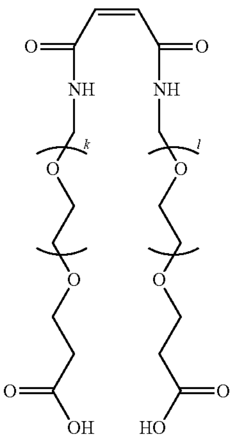

wherein n, k and l are independently 0, 1, 2, 3, 4, 5, 6, 7, 8, 9 or 10.

2. The method of claim 1, wherein the olefin production plant produces olefin by steam cracking of a hydrocarbon feed.

3. The method of claim 2, wherein the hydrocarbon feed is naphtha, liquid petroleum gas, ethane, butane, or any combination thereof.

4. The method of claim 2, wherein the hydrocarbon feed is liquid petroleum gas, ethane, propane, butane, or any combination thereof.

5. The method of claim 2, wherein the hydrocarbon feed is naphtha, liquid petroleum gas, propane, butane, or any combination thereof.

6. The method of claim 2, wherein the hydrocarbon feed is naphtha, ethane, propane, butane, or any combination thereof.

7. The method of claim 2, wherein the hydrocarbon feed is naphtha, liquid petroleum gas, ethane, propane, or any combination thereof.

8. The method of claim 1, wherein the aqueous system is a dilution steam system.

9. The method of claim 1, wherein the PEG functionalized maleamide is added to a process water stripper unit of the dilution steam system.

10. The method of claim 9, wherein the PEG functionalized maleamide is added to a bottom portion of the process water stripper unit.

11. The method of claim 1, wherein the water soluble adduct is a water soluble polymer.

12. The method of claim 1, wherein the one or more fouling precursor compounds are styrene, indene, divinylbenzene, methyl styrene, or cyclopentadiene, or any combination thereof.

13. The method of claim 1, further comprising removing the water soluble adduct from the aqueous system.

14. The method of claim 13, wherein the aqueous system is a dilution steam system and the water soluble adduct is removed from a process water of the dilution steam system by a blow down process.

15. The method of claim 1, further comprising:

determining amount of the fouling precursor compound present in the aqueous system; and adding the PEG functionalized maleamide to the aqueous system such that weight ratio of the added PEG functionalized maleamide to the fouling precursor compound is 0.25:1 to 1.2:1.

16. The method of claim 15, wherein the fouling precursor compound is styrene.

17. The method of claim 16, wherein weight ratio of the added PEG functionalized maleamide to styrene is 0.25:1 to 1:1, and wherein the aqueous system is a dilution steam system.

18. The method of claim 1, wherein the PEG functionalized maleamide is dosed continuously.

* * * * *